United States Patent
Bandura et al.

(10) Patent No.: US 9,700,245 B2
(45) Date of Patent: Jul. 11, 2017

(54) TRANSDERMAL ANALYTE EXTRACTION AND DETECTION SYSTEM AND THE METHOD THEREOF

(75) Inventors: Bhaskara Rao Bandura, Andhra Pradesh (IN); Radhakrishnan Ramdas, Andhra Pradesh (IN); Krishnamohan Sharma, Andhra Pradesh (IN); Kartik Karri, Andhra Pradesh (IN)

(73) Assignee: ITRACE BIOMEDICAL INC., Milpitas, CA (US)

( * ) Notice: Subject to any disclaimer, the term of this patent is extended or adjusted under 35 U.S.C. 154(b) by 0 days.

(21) Appl. No.: 13/428,670

(22) Filed: Mar. 23, 2012

(65) Prior Publication Data
US 2013/0079605 A1    Mar. 28, 2013

(30) Foreign Application Priority Data
Sep. 23, 2011 (IN) .......................... 3307/CHE/2011

(51) Int. Cl.
*A61B 5/00* (2006.01)
*A61B 5/145* (2006.01)
(Continued)

(52) U.S. Cl.
CPC ........ *A61B 5/14514* (2013.01); *A61B 5/1477* (2013.01); *A61B 5/1486* (2013.01); *A61B 5/6833* (2013.01)

(58) Field of Classification Search
CPC ............... A61F 9/00745; A61B 5/1455; A61B 5/14552; A61B 5/150053; A61B 5/145; A61B 5/14507; A61B 5/1451; A61B 5/1486; A61B 5/1491

USPC ....... 600/309, 310, 316, 322, 323, 326, 340, 600/344, 473, 476, 345; 422/82.01, 422/82.02, 82.05; 435/14, 25, 176, 287.1, (Continued)

(56) References Cited

U.S. PATENT DOCUMENTS

| 4,286,592 A | 9/1981 | Chandrasekaran |
| 4,404,460 A | 9/1983 | Kerr |

(Continued)

OTHER PUBLICATIONS

Park et al., "The effect of heat on skin permeability", International Journal of Pharmaceutics, 2008, vol. 359, p. 94-103.
(Continued)

*Primary Examiner* — Eric Winakur
*Assistant Examiner* — Chu Chuan (JJ) Liu
(74) *Attorney, Agent, or Firm* — Kilpatrick Townsend & Stockton LLP

(57) ABSTRACT

The present invention relates to an active transdermal analyte detection system performing extraction and detection of body analytes comprising of a patch accepting at least one electrical input; a plurality of transducers configured for converting input electrical energy to different forms of energies for activating extraction procedure; a controller configured for providing the control signals, intensity, sequence, nature, and timing information for the different energies supplied to the said patch vide said transducers; and at least one layer/compartment configured for either collection of extracted fluids and/or delivering at least one reagent formulation that detects the body analyte on activation and a method for performing transdermal extraction and detection of body fluids using said electronic patch.

32 Claims, 3 Drawing Sheets

Figure 1:
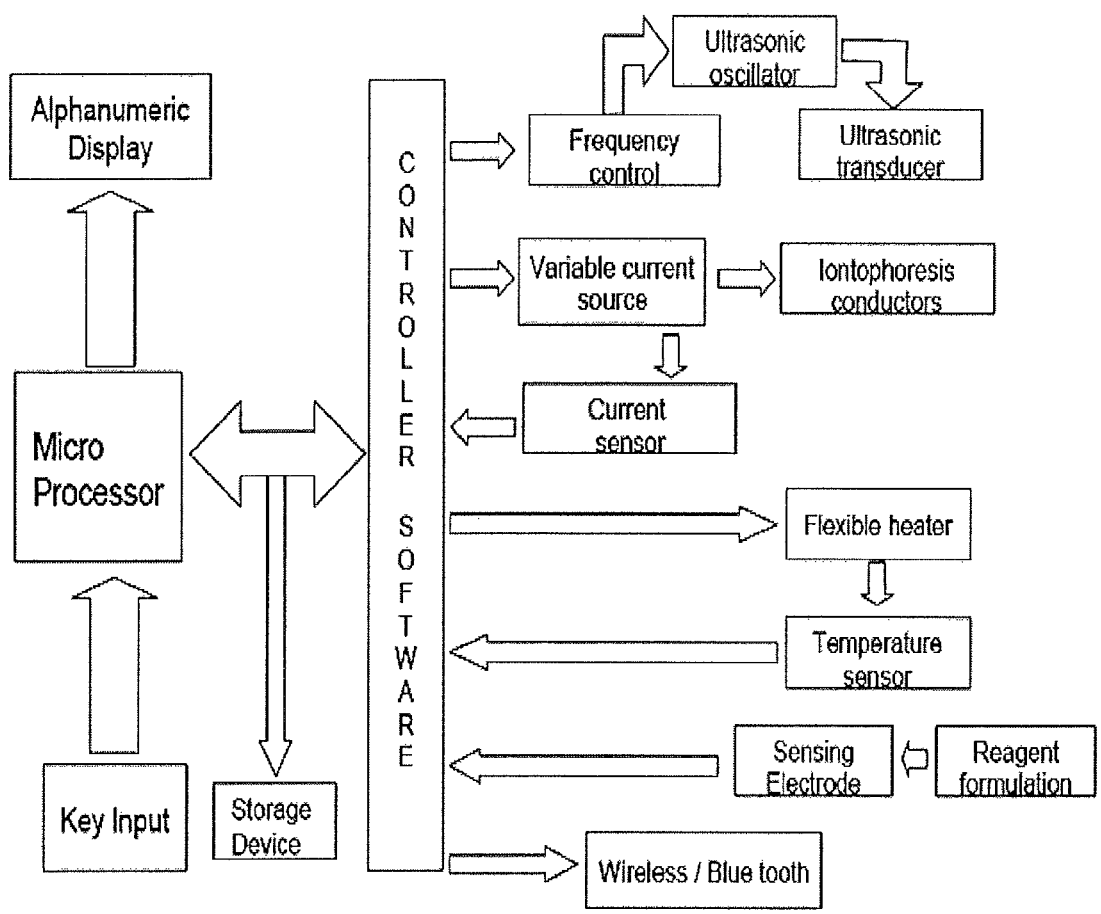

Block Diagram of Extraction and Detection System

(51) Int. Cl.
  *A61B 5/1477* (2006.01)
  *A61B 5/1486* (2006.01)

(58) Field of Classification Search
  USPC .......... 435/817; 436/15, 149, 151, 518, 525,
                  436/806; 604/22; 424/402
  See application file for complete search history.

(56) References Cited

U.S. PATENT DOCUMENTS

| | | | |
|---|---|---|---|
| 4,736,088 A | 4/1988 | Bart | |
| 4,823,775 A | 4/1989 | Rindt | |
| 5,036,861 A | 8/1991 | Sembrowich et al. | |
| 5,076,273 A | 12/1991 | Schoendorfer et al. | |
| 5,139,023 A * | 8/1992 | Stanley et al. | 600/368 |
| 5,140,985 A | 8/1992 | Schroeder et al. | |
| 5,279,543 A | 1/1994 | Glikfeld et al. | |
| 5,421,816 A | 6/1995 | Lipkovker | |
| 5,658,247 A | 8/1997 | Henley | |
| 5,667,487 A | 9/1997 | Henley | |
| 5,697,896 A | 12/1997 | McNicholas et al. | |
| 5,722,397 A * | 3/1998 | Eppstein | 600/345 |
| 5,833,647 A | 11/1998 | Edwards | |
| 5,860,857 A | 1/1999 | Wasastjerna et al. | |
| 5,860,957 A | 1/1999 | Jacobsen et al. | |
| 5,902,603 A | 5/1999 | Chen et al. | |
| 5,935,598 A | 8/1999 | Sage et al. | |
| 5,947,921 A * | 9/1999 | Johnson et al. | 604/22 |
| 5,948,012 A | 9/1999 | Mahaffey et al. | |
| 6,142,939 A | 11/2000 | Eppstein et al. | |
| 6,180,416 B1 * | 1/2001 | Kurnik et al. | 600/316 |
| 6,190,315 B1 | 2/2001 | Kost et al. | |
| 6,251,083 B1 * | 6/2001 | Yum et al. | 600/309 |
| 6,261,595 B1 | 7/2001 | Stanley et al. | |
| 6,334,856 B1 | 1/2002 | Allen et al. | |
| 6,527,716 B1 | 3/2003 | Eppstein | |
| 6,572,871 B1 * | 6/2003 | Church | A61K 9/70 424/402 |
| 6,623,457 B1 | 9/2003 | Rosenberg | |
| 6,649,886 B1 | 11/2003 | Kleshchik | |
| 6,662,044 B2 | 12/2003 | Crawford et al. | |
| 6,692,456 B1 * | 2/2004 | Eppstein et al. | 600/316 |
| 7,483,738 B2 | 1/2009 | Tamarkin et al. | |
| 7,650,177 B2 * | 1/2010 | Hoarau et al. | 600/344 |
| 9,327,105 B2 | 5/2016 | Ramdas et al. | |
| 2002/0055702 A1 | 5/2002 | Atala et al. | |
| 2002/0114827 A1 | 8/2002 | Zhang et al. | |
| 2002/0156415 A1 | 10/2002 | Redding | |
| 2003/0023151 A1 * | 1/2003 | Khalil et al. | 600/309 |
| 2003/0032900 A1 | 2/2003 | Ella et al. | |
| 2003/0100846 A1 * | 5/2003 | Custer | A61B 5/14514 600/573 |
| 2003/0208113 A1 * | 11/2003 | Mault et al. | 600/316 |
| 2003/0225360 A1 | 12/2003 | Eppstein et al. | |
| 2004/0073079 A1 | 4/2004 | Altshuler et al. | |
| 2005/0283110 A1 | 12/2005 | Atala et al. | |
| 2006/0058709 A1 | 3/2006 | Mason et al. | |
| 2007/0083186 A1 | 4/2007 | Carter et al. | |
| 2007/0265664 A1 | 11/2007 | Gerber et al. | |
| 2009/0069041 A1 | 3/2009 | Kitazoe | |
| 2010/0081971 A1 | 4/2010 | Allison | |
| 2010/0114252 A1 | 5/2010 | Torgerson | |
| 2010/0217349 A1 | 8/2010 | Fahey et al. | |
| 2011/0264028 A1 | 10/2011 | Ramdas et al. | |
| 2014/0200487 A1 | 7/2014 | Ramdas et al. | |
| 2014/0244292 A1 | 8/2014 | Rosenberg et al. | |
| 2014/0343628 A1 | 11/2014 | Kaula et al. | |

OTHER PUBLICATIONS

Non-Final Office Action for U.S. Appl. No. 13/064,334, mailed on May 16, 2013, 21 pages.
Final Office Action for U.S. Appl. No. 13/064,334, mailed on Oct. 16, 2013, 19 pages.
Non-Final Office Action for U.S. Appl. No. 13/064,334, mailed on Mar. 24, 2014, 18 pages.
Final Office Action for U.S. Appl. No. 13/064,334, mailed on Aug. 12, 2014, 20 pages.
International Patent Application No. PCT/US2016/015984, "International Search Report and Written Opinion Received", Apr. 18, 2016, 14 pages.

* cited by examiner

Block Diagram of Extraction and Detection System

Schematic cross section of the Transdermal patch

Possible electrode designs

3(a)　　　　3(b)　　　　3(c)　　　　3(d)　　　　3(e)

TRANSDERMAL ANALYTE EXTRACTION AND DETECTION SYSTEM AND THE METHOD THEREOF

RELATED APPLICATIONS

The present application is based on, and claims priority from, Indian Application No. 3307/CHE/2011 filed Sep. 23, 2011, the disclosure of which is hereby incorporated by reference herein in its entirety.

FIELD OF INVENTION

The present invention generally relates to a novel & versatile transdermal analyte extraction/detection system and the method thereof. More particularly, the present invention discloses a system and a programmable method for transdermal withdrawal of bodily fluids from the skin of the patient/user which utilizes a controller for providing electrical (iontophoretic, electrophoretic), sonic, and heat energies in combination and/or in sequence across the skin and/or any biological tissue. Further, the extracted bodily fluids are chemically, and/or electronically and/or spectroscopically analyzed to detect the targeted analytes.

BACKGROUND ART

Conventional diagnostic tests are performed on humans to evaluate the amount or existence of analytes in the blood, which requires drawing of a blood sample. Typically, blood samples are removed from a subject either by using a syringe or by pricking the skin. This involves pain and inconvenience, and may cause patients to miss monitoring routines. One blood/body analyte of interest is blood glucose with quantitative analysis done using enzymatic method with Glucose Oxidase (GOx). The amount of blood drawn, of course, depends upon the amount of blood required for testing. Thereafter, the blood sample may be prepared and specifically tested for a variety of substances using techniques well known in the art. To overcome the problems associated with the invasive techniques, several approaches have been proposed that involves collection/extraction of analytes through the skin/biological membrane by enhancing its permeability.

Several techniques are employed to enhance the permeability of the biological membrane, such as creating physical micropores, physically disrupting the lipid bilayers, chemically modifying the lipid bilayers, physically disrupting the stratum corneum, and chemically modifying the stratum corneum. The creation of micropores, or the disruption thereof, may be achieved by physical penetration, using a heat source, an ultrasonic needle, an ultrasonic transducer, cryogenic ablation, RF ablation, photo-acoustic ablation, a needle, a microneedle, a laser, and combination thereof.

Although these methods can be used for extraction of body fluids, there are certain limitations that may apply when applied to human skin. For example, a major limitation is the flow and volume of body fluid that can be transported across the stratum corneum. In general, high-pressure force is necessary in order to transport fluid across an enhanced permeable area of stratum corneum. The application of vacuum on skin for an extended period may cause physical separation of the epidermis from the dermis result in bruises and blisters.

Over the last few years, methods of determining the concentration of blood glucose or other substances without drawing blood have been developed. For example, Stanley U.S. Pat. No. 5,139,023 describes a transdermal glucose monitoring apparatus that uses a permeability enhancer, such as a natural bile salt, to facilitate transdermal movement of glucose along the concentration gradient between the higher glucose concentration in the interstitial fluid and the lower glucose concentration in the receiving medium. In some embodiments, the receiving medium is the aqueous portion of a hydrogel support adhered to the subject's skin. Stanley measured the glucose concentration within the hydrogel by removing the hydrogel from the subject's skin, placing the hydrogel in water and letting the glucose diffuse out of the hydrogel into the water. The water was then analyzed for glucose concentration.

Sembrowich U.S. Pat. No. 5,036,861 describes a glucose monitor that collects the subject's sweat through a skin patch attached to the subject's wrist.

Sembrowich describes the use of iontophoresis to transdermally introduce a gel into the subject's skin. The gel contains a cholinergic agent for stimulating the secretion mechanism of the eccrine sweat gland and agents that minimizes or prevents loss of glucose from the sweat as it travels from the sweat gland to the skin patch.

The Sembrowich device uses electrodes to measure the glucose level in the collected sweat by some unspecified method.

Schoendorfer U.S. Pat. No. 5,076,273 describes a method and apparatus for determination of chemical species in body fluid. Sweat expressed from the subject's skin is collected in a patch adhered to the subject's skin. The patch concentrates the sweat in a binder layer by driving off a portion of the collected water. The collected analyte binds with a specific binding partner in the patch to present a visual indication of its presence in the patch.

Schroeder U.S. Pat. No. 5,140,985 discloses a sweat-collecting device mounted on a subject. The device has an electrode-based glucose detection system that can give a qualitative indication of blood glucose concentration.

Glikfeld U.S. Pat. No. 5,279,543 describes the use of iontophoresis to sample a substance through skin into a receptor chamber on the skin surface. In one embodiment, Glikfeld describes an in vitro device consisting of two gel electrodes attached to one side of hairless mouse skin. Radiolabeled glucose is placed on the other side of the skin, and current is applied to the electrodes for a period of time. The electrodes are then analyzed for radioactivity content by conventional liquid scintillation counting.

In general, non-invasive analyte detection systems known in the literature have limitations in withdrawal/extraction of targeted body fluids in desired quantities and thereby have detection accuracy/reliability related issues and often their detection response time is unacceptably slow. For these reasons, non-invasive analyte detection methods for therapeutic purposes have not yet become commercially viable.

For example, iontophoresis and variety of individual energy forms (including an array of microneedles) have been used to transport the body fluid across the skin membrane involving multitude of transport mechanisms. However each energy form has its own preferred transport mechanism and may have limitations with regard to the quantity, and type of fluid they could extract across the skin membrane. Besides the fluid permeation rates dramatically vary depending upon the nature of energy form applied. In this regard, we propose the use of a single controller that provides a combination of energy sources/pulses to act upon a transdermal patch (which may include microneedles) with varying intensity, sequence, and timing to enable the transport of fluids using synergistic/cooperative transport mechanisms. As a consequence, application of multiple energy forms in a predetermined sequence/time intervals and intensities provides an excellent opportunity to permeate body fluids containing analytes in adequate quantities rapidly, and thus provide precise control over the analyte detection. It is also possible to pull the analytes of interest selectively along with the body fluids by permeating suitable counter ions with Iontophoresis. Further, the extraction of body fluids through multiple energies could be complemented by application of a negative pressure/vacuum for enhancing detection accuracy.

In this venture, we take advantage of printed electronics/microneedle arrays to extract and/or collect body fluid transdermally using a combination of transport mechanisms and energy sources, i.e., heat, sound and electromotive force, where a microprocessor controls the thermal/ultrasonic energy and electrical current applied to the skin in a programmable fashion (concurrently or alternately) for body fluid extraction and detection applications. A modified version of the transdermal patch system reported here could be used for transdermal drug delivery across the skin, while using a similar controller that provides combination of energy sources (Patent No: 819/CHE/2010, An Active Transdermal Drug Delivery and The Method Thereof). One such interest is transdermal delivery of Insulin.

Further, the disclosure is intended to generate a new versatile active transdermal patch for extracting a variety of analytes along with body fluids with controlled transportation rates and quantities to enable on demand detection of the analytes. Current active transdermal non-invasive patches rely on unregulated or inadequate quantities of body fluids that impose several limitations on accurate detection of analytes in prescribed/required time intervals for reliable medical diagnostics of practical utility.

SUMMARY OF THE INVENTION

The proposed disclosure is intended to generate a new disposable active transdermal patch for withdrawal/extraction of adequate quantities of body fluids for detecting the analyte (especially, blood glucose) in such a way that the detection accuracy/reliability is not compromised, and the detection response time is rapid for therapeutic applications. Further, the energy pulses provided by the controller enable rapid reaction between body fluids and chemical reagents/enzymes to produce rapid signal for analyte detection and reduce signal to noise ratio.

Using the present invention, we herein disclose the development of a novel active transdermal patch (including microneedle based arrays) that extracts/collects the body fluids (e.g. interstitial fluids) using a combination of energy sources such as heat, sound and electricity (i.e., iontophoresis or electroporation) synergistically, to accomplish the enhanced skin permeability on a single platform for targeted analyte detection, preferably blood glucose. The detection methodology includes either chemical, enzymatic, and spectrophotometric or a combination thereof, for a specific analyte.

Therefore such as herein described there is disclosed an active transdermal analyte detection system performing extraction and detection of body analytes comprising of: a patch accepting at least one electrical input; a plurality of transducers configured for converting input electrical energy to different forms of energies for activating extraction procedure; a controller configured for providing the control signals, intensity, sequence, nature, and timing information for the different energies supplied to the said patch vide said transducers; and at least one layer/compartment configured for either collection of extracted fluids and/or delivering at least one reagent formulation that detects the body analyte on activation.

Whereas the present invention provides a method for transdermal body fluid extraction, which overcomes the problems associated with available non-invasive transdermal analyte detection systems, such as poor analyte detection accuracy, low reliability and slow response time, by the use of multiple energies (heat, sound and reverse iontophoresis) that increase the permeability of the body fluids to the surface of the skin, thus extracting considerably higher quantity of body fluids in shorter time. Further, the energy pulses also improve the reaction between chemical reagents and body fluids and provide faster and reliable read outs. The skin patch, which will be in contact with the skin, contains either a formulation for enzymatic and chemical detection, or an optical system and associated electronics for spectroscopic detection of the body analytes.

Also herein disclosed a method for performing transdermal extraction and detection of body fluids using an electronic patch comprising the steps of: attaching the patch to the skin of the subject; inputting electrical energy from a power source; controlling the electrical energy power input using a controller; converting the electrical energy to different forms of energy using a plurality of configured circuit blocks; delivering different forms of energy using a plurality of suitable transducers; controlling the intensity, sequence, nature, and timing signals for activating the different energies supplied to the said patch; activating the extraction procedure for analyte using at least one energy; and detecting and/or collecting the extracted analyte.

Therefore the primary object of the present invention is to provide an active transdermal skin patch driven by a controller that provides a combination of energy sources/pulses with varying intensity, sequence, and timing to enhance skin permeability for the transport of body fluids in sufficient quantities/permeation rates for accurately detecting the analytes of interest for medical diagnostics.

Any analyte that can be transdermally extracted through the proposed skin patch is quantified; one analyte of particular clinical and therapeutic interest is glucose, other analytes include, but are not limited to electrolytes such as lithium, sodium, potassium and calcium; toxins; lipids such as cholesterol; hormones such as insulin; therapeutic and pharmacologic agents; drugs of abuse; amino acids; blood gases; enzymes, antibiotics, cytokines and other biologically relevant molecules. Following extraction, detection and quantitation of the analyte may be carried out by any standard chemical, physical, enzymatic and/or optical means.

The skin permeability response to the application of combination of energy source pulsing sequences/intensities in tandem are optimized experimentally to develop the best possible profile for a given analyte extraction/detection. In general, we found that application of two or three distinct energies simultaneously or synergistically enhances the permeation rate almost 200 fold compared to control and/or a single energy pulse. Further, the onset of body fluid migration is proven to be quite rapid. Therefore, the body fluid extraction could be highly customized for a given analysis and may enable the patient/physician to provide proper customized analyte detection conditions to meet the kinetic profile of the fluids for individual patient needs.

It is an object of the present invention to provide an electronically controlled versatile body fluid extraction and detection system.

It is another object of the present invention to provide a body fluid extraction method and a system configured to control the energies (intensity and sequence) such as heat, ultrasound (sonophoresis), reverse iontophoresis and negative pressure, and combination thereof.

It is another object to provide a body fluid extraction method and system that can be programmed and used for the detection of single or multiple analytes at one time or at periodic intervals.

It is another object of the present invention to provide a non invasive transdermal body fluid extraction system having inbuilt analyte collection and detection system or an analyte collection system to collect the sample. The collected sample can be analyzed remotely either enzymatically, chemically, or optically for the specific analyte.

It is another object of the present invention to provide a non invasive transdermal body fluid extraction and detection system that can store the collected analyte data and transmit it to the computer or to the physician.

It is another object of the present invention to provide sensors for feedback on patient status, enabling the controller to commence the fluid extraction and perform the analysis.

As per an exemplary embodiment of the present invention there is provided an active transdermal patch with or without microneedle arrays that transdermally extracts body fluids by application of electric pulse, heat, sound or a negative pressure over the stratum corneum (SC) by accepting combination of energy pulses from a controller comprising an energy source (battery/capacitor), a microprocessor and related electronics, along with the required software that controls the intensity, sequence and timing of energies supplied to the active transdermal detection patch for greatly enhancing the skin permeation for the body analytes for extraction and capable of detecting body analytes.

The active transdermal patch described above further includes a reservoir as part of it. The reservoir of the transdermal patch contains gel or hydrogel or an absorbent material upon to which the reagent material can be entrapped or attached by ionic and/or covalent means or by adsorption to detect the presence of certain analytes in the body fluid that has been extracted through the biological membrane.

It is one of the objectives of the present invention that the extracted analyte reacts with the reagent present in the reservoir and gives by-products which can be detected using electrical, electrochemical, enzymatical, or optical signal means.

In one embodiment of the present invention, along with the multiple energies, osmotic force is being used to enhance the extraction of the body analyte. The osmotic agent present in the formulation of the reservoir comes in contact with the biological membrane when the patch is attached to the skin. The osmotic force generated depends on the concentration of the osmotic agent present in the reservoir of the patch.

In one embodiment of the present invention, chemical enhancers are used to enhance the permeation of the biological membrane. The formulation in the patch reservoir contains these chemical enhancers. These come in contact with the biological membrane when the patch is attached to it. The chemical enhancers increase the permeation of analyte by increasing the capillary action of the biological membrane.

It is an additional object of the present invention to provide an improved versatile active transdermal patch which is small, flexible and adherent that can cover the desired dermal area more efficiently and conveniently without any leakages.

To achieve the foregoing objectives and in accordance with the present invention as embodied and broadly described herein, the present invention discloses a transdermal body fluid extraction and detection system comprising of an active patch, a microprocessor based controller, at least one electrical energy power input, a plurality of circuit modules in the controller for converting electrical energy to different forms of energy, and a plurality of transducers for transferring these energies to the skin through the patch. The microprocessor based controller will be configurable for providing the intensity, sequence, nature, and timing information for the different energies supplied to the said patch. The said controller will have a storage device for storing the collected detection data.

Further embodiment of the present invention provides a support material for transdermal patch which is a thin flexible sheet made of polymer, or rubber, or resin, or textile, or thin metal, acceptable for medical applications. At least a part of the support material has some kind of adhesive to stick it to the skin.

It is an embodiment of the present invention that has a size selective semipermeable membrane to increase the accuracy of the detection by minimizing the interferences from the other body analytes, especially in case of glucose detection. The semipermeable membrane is configured to be part of the patch, and comes in direct contact with the skin, when stuck on the skin. The extracted body fluid from the permeabilized skin passes through the size selective membrane, which allows only the target analytes (e.g. Glucose molecule) of the specific size range to pass through and react with the reagents in the formulation.

A further embodiment of the present invention provides a support material (metal, metal oxide or polymer) that has an array of microneedles. The tips can be anything from tapered-conical to chiseled to beveled. The needles can vary in lengths from 150 µm to even 1500 µm. The tip diameter of 10-300 µm. Ideally, the microneedles will only penetrate deep enough to pass the first ~15 µm of skin, the barrier known as the stratum corneum.

A further embodiment of the present invention is to include a timer circuitry in the controller for regulating the extraction requirements to ensure the safety of patients.

A further embodiment of the present invention, the controller provides a feedback control mechanism which provides fine control over the extraction of the body fluids along with the analysis using different analytes.

A further embodiment of the present invention provides sensors in the active transdermal patch and enable data collection to the feedback control mechanism and the controller.

Additional objects and the advantages of the invention will be set forth in the description which follows and in part will be obvious from the description or may be learned by the practice of the invention. The objects and the advantages of the invention may be realized and obtained by means of the instruments and combinations particularly pointed out in the appended claims.

BRIEF DESCRIPTION OF THE ACCOMPANYING DRAWINGS

Figure 2A:
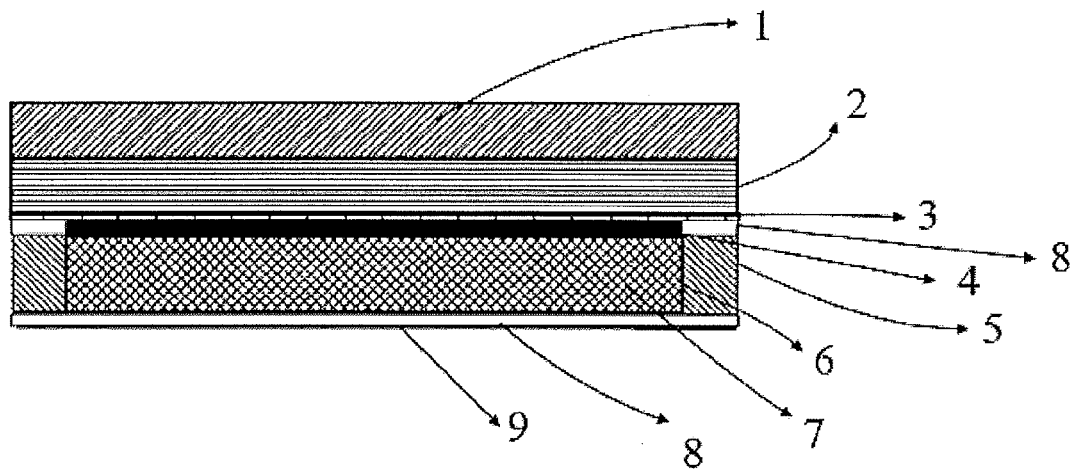
Figure 2B:
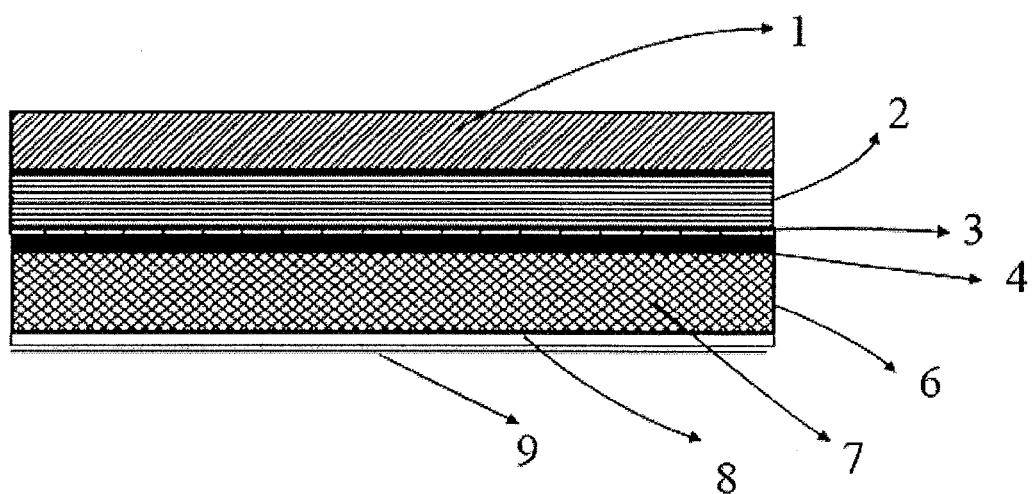

FIG. 1 illustrates schematic block diagram of active analyte extraction/detection system and various components present in it in accordance with the present invention;

FIGS. 2(a) and 2(b) illustrates the schematic cross section of the transdermal patch, various components present in it and different layers in accordance with the present invention;

FIGS. 3(a), 3(b), 3(c), 3(d), and 3(e) illustrate the schematic representation of electrodes of the analyte extraction/detection system in accordance with the present invention.

DETAILED DESCRIPTION

The transdermal extraction of analytes provides several important advantages over traditional intravenous extraction routes as it avoids the inconvenience, permits steady extraction of analytes over longer time periods and enables both on-site and off-site detection. The extraction of the analytes is carried out by a combination of energy sources such as heat, ultrasound, and electricity (i.e., iontophoresis or electroporation) synergistically to accomplish the enhanced skin permeability on a single platform. The detection may include either chemical, enzymatic, and spectrophotometric or combination methods for a specific analyte. The said energy sources are applied on the skin using a skin patch, which will be in contact with the skin, containing either a formulation for enzymatic and chemical detection or an optical system for spectroscopic detection of the body analytes.

Any analyte that can be extracted through the permeabilized skin may be quantitated. The analytes of clinical and therapeutic interest are glucose, lithium, sodium, potassium and calcium; toxins; lipids such as cholesterol; hormones such as insulin; therapeutic and pharmacologic agents; drugs of abuse; amino acids; blood gases; enzymes, antibiotics, cytokines and other biologically relevant molecules. Following extraction, detection and quantitation of the analyte will be carried out by any standard chemical, physical, enzymatic and/or optical means.

The stratum corneum, the outer layer of the skin, is a complex structure of compact keratinized cell remnants separated by lipid domains and is responsible for the well known barrier properties of the skin, i.e., transdermal flux of ions, drugs or other molecules into the body and out of the body. The stratum corneum is continuously renewed by shedding of corneum cells during desquamation and the formation of new corneum cells by the keratinization process.

The transport across the skin barrier can be enhanced by a controller that provides a combination of energy sources/pulses with varying intensity, sequence, and timing, especially to collect body fluids in sufficient quantities for accurately detecting the analytes of interest for medical diagnostics. The energy pulses include thermal force, sonophoretic, and iontophoretic. Further, pressure, vacuum, chemical enhancers and osmotic forces may complement above energy pulses.

The skin permeability response to the application of a combination of energy sources and their pulsing sequences/intensities in tandem is optimized experimentally to develop the best possible profile for a given analyte extraction. Therefore, the body fluid extraction could be highly customized for a given analysis, and enables the patient/physician to provide properly customized analyte detection conditions to meet the kinetic profile of the body fluids for individual patient needs.

Figure 3:
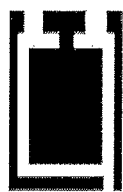
Figure 3:
Figure 3:
Figure 3:
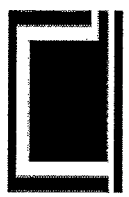
Figure 3:

Iontophoresis requires the use of electrodes containing oxidation-reduction species as well as passing electric current through the skin. A DC field is used to transport molecules through the stratum corneum via appendageal or paracellular space. The preferably used electrode design is illustrated in FIG. 3.

Ultrasound can be applied to the stratum corneum to disrupt the lipid bilayers between the keratinocytes through the action of cavitation and its bioacoustic effects. The disruption of stratum corneum, a barrier to transport, allows the enhanced diffusion of analyte, such as glucose or drugs, through, into, and out of the skin.

Transport of analytes and body fluids is enhanced further by the action of heat, which increases the permeability of the skin by disordering the stratum corneum lipid structure, by disruption of stratum corneum keratin network structure, and by decomposition and vaporization of keratin to create micron-scale holes in the stratum corneum.

Heat induced extraction increases kinetic energy of the analyte cells, proteins, lipids, and carbohydrates in the cell membrane to promote the skin permeability, body fluid circulation, and blood vessel wall permeability. It is also possible to use focused thermal energy in short bursts to porate the skin (thermal ablation of stratum corneum).

Electricity (e.g., iontophoresis) propels charged analytes across the skin barrier transdermally in the presence of an electric field, where the repulsive electromotive forces enable mass extraction. The preferred transport pathway is expected to be through the routes of least electrical resistance. A number of factors influence iontophoretic transport; including current, voltage, time applied, skin pH, reservoir size, charge, concentration of the analyte, presence of competing ions, permeation enhancers, area of the patch, and integrity of the skin/patch interface. However, the significance of many of these factors will alter when heat and/or ultrasound energy is combined with the electromotive force. The preferred sequence of energy pulses applied (sequentially and/or simultaneously) on a given skin sample vide a patch identifies an experimentally determined/programmable pulsing sequence to optimize/maximize analyte permeation. In this way, one can accomplish rapid onset or offset for analyte extraction (for a variety of analytes) in a highly controllable and programmable fashion. The proposed active analyte extraction technology enables the extraction of analytes that are hard to permeate through skin by means of a motive force. These motive forces include, thermal, sonophoretic, iontophoretic forces and the use of these active forces provides a means for obtaining fluid for subsequent analysis.

The transport of body analytes across the biological membrane is also enhanced by the use of chemical enhancers. Transport enhancement through stratum corneum is obtained by adding capillary permeability enhancers, for example, histamine. These agents are delivered across the biological membrane during application of external energy in the form of heat, ultrasound and/or iontophoresis in combination and/or sequentially, cause local edema that increases local fluid pressure and enhances the transport of analytes across the biological membrane. In addition, the occurrence of free fluid due to the edema induces cavitation locally so as to enhance transport of analytes across the biological membrane.

FIG. 1 shows a schematic block diagram of the proposed analyte extraction and detection system. The power is provided by a battery or capacitor of a suitable power supply unit. The controller comprises microprocessor unit and controls a plurality of electronic circuit modules for the generation of different energy forms like heat, ultrasound and current for iontophorosis. The controller as disclosed herein is programmed for the duration, switching sequence and intensity of each of these energies. Suitable transducers are connected to the controller for delivering these energies to the skin. The controller is also connected to a plurality of sensor transducers for the purpose of feedback and control. The sequencing of the various layers could be altered and does not necessarily have to be in the order as shown in figures. The above-mentioned transducers can either be part of the transdermal patch or exogenous to it.

FIG. 2 illustrates the schematic cross section of the skin patch along with possible positions of the transducers in the proposed extraction and detection system. The ultrasonic transducer (1) is placed at the top, followed by the heating patterns (2). The heater comprises of resistive and/or inductive patterns perform as heating elements. The electrodes (4) are printed on a flexible support material, which acts as a backing layer (3), are placed very near to the formulation compartment (6) touching the material present in the compartment for the activation of iontophoresis and electrochemical reaction. The purposes of the compartments are described in detail in the subsequent description. Medicated foam material (5) forms the outline of the compartment and helps in preventing the spreading of the formulation. The compartment comprises of reagent formulation/absorbent material (7) used for the detection and the extraction/collection of analyte processes. The detection formulation is present just above the skin so that the analyte detection is carried out as and when the analyte is being extracted from the skin. The different transducers configured for providing different kind of energies when triggered by the controller are held together by a support material. The bottom portion of the said system comprises of a non-irritant adhesive (8) helps the system to remain in contact with the skin when in use and a Release liner (9) which will be removed from the system before sticking it to the skin. In some cases the reagent formulation (7) itself is an adhesive matrix and doesn't require adhesive (8).

FIG. 3 illustrates the different possible electrode designs. The electrodes (working electrode, counter electrode and reference electrode) are designed for the application of iontophoretic current for analyte extraction in a controlled fashion, as well as having an active role in the detection process as described earlier.

The sequencing of the various layers could be altered and does not necessarily have to be in the order as shown in figures. In an exemplary embodiment the patch also comprises of at least one light source for the aforesaid spectroscopic analysis. In other embodiment the patch includes a plurality of light sources working in combination/independently controlled by the controller for spectroscopic detection of analytes. The light source may be a light emitting diode and/or a laser, emitting light in the infrared, visible or ultraviolet spectrum, depending on the nature of the analyte being analyzed. In another exemplary embodiment the detection is programmed based on analyte, time, computed electrical energy generated and skin permeability. In the process of the detection of the analyte, and under condition of the mixing of the reagent formulation with the extracted analyte, it has been noticed that an electrical energy is released during the course of reaction between the analyte (glucose) and the reagent (glucose oxidase) present in the formulation. The electrical energy generated is being measured by the controller and thereby analysis results could be procured instantly.

Further, multiple layers/components (at least two or more) of the patch could be embedded into a single layer or could be from physically distinct layers (exogenous). Also the detection formulation layer could be a reservoir cell, or part of coating formulation (including polymeric binders, excipients, and adhesive matrix) or a membrane matrix or hybrid form of the above.

The system includes four major components: a source of power and a microprocessor based controller, a plurality of electronic circuit blocks for creation and control of different energies, a plurality of transducers for transferring the said energies to the skin, and the transdermal patch, as described above.

The power source can be a battery or a suitable AC to DC adapter, or a capacitor providing 0-12V DC at 0.01 mA to 1000 mA. There will also be a provision for an electronic circuit to raise the voltage and charge the capacitor, which in turn will be discharged through suitable electrodes for electroporation, if required. This section is provided with an on/off/standby switch to conserve energy when not in use. The standby function is optionally automated based on the program in the controller.

The controller has a microprocessor containing the required software for operation. A suitable keypad and display is provided for human interaction through a menu. The main function of the controller unit is to control the sequence, intensity and duration of the energy forms described earlier in association with the electronic circuit blocks which will be described in the following sections, interface with the detecting transducers and do the required computation for quantifying the detected analyte, and other related housekeeping functions. In an embodiment the various forms of energy that are supplied to the patch vide a combination effect of control signals controller and the transducer are supplied in the form of pulses with a minimum duration of 1 millisecond or more.

The controller is described in particular with blocks for a better understanding and in not with a view to limit its functions in any way. The controller herein described is a programmable controller and the different functionalities of the controller are preloaded or may be programmed onsite. One of the electronic circuit blocks is for the generation of controlled heat. This block consists of an electronic switch controlled by signals from the controller. This block also contains a subsystem that monitors the temperature and relays the same information to the controller. Based on the settings and the program running in the controller, the exact temperature and duration of application of heat can be precisely controlled by this circuit block. This block uses a heating element as a transducer. The said heating element can be printed, flexible, or of any other suitable type configured for a scale of temperatures with fixed upper and lower limits. Another transducer used by this block is a temperature sensor integrated circuit, used for the feedback mechanism. The temperature, duration and sequence are all controlled by signals from the controller. The system uses high resistance patterns for converting electrical energy into heat energy between 25 and 200° C. and preferably 30 to 60° C. The preferred range for the heat energy for the active patch disclosed herein is 50° C. or close to the temperatures that is user/patient compliant. In some instances, temperature could be higher than 50° C. to further enhance the permeation of body fluids, but the time duration for high heat exposure in such instances is so short that patient would not feel the sensation or discomfort.

Another circuit block that is reusable is used for the generation of ultrasonic frequency oscillations. This block takes input from the controller and generates ultrasonic frequencies in the range 20,000 to 25,000 Hz. A subsystem of this functional block amplifies the generated oscillations in a controlled manner. This circuit block uses a piezoelectric quartz crystal/polymer/ceramic transducer to supply the ultrasonic energy to the skin. The duration, sequence and amplitude of the output are all controlled by signals from the controller.

Another circuit block is used for supplying and controlling the current for iontophoresis. This block has an electronic switch and a programmable current control mechanism. This block can be set either for constant current operation, or the maximum permissible current can be set. The normal working range is 0.01 to 10 milli ampere. A couple of conductive electrodes are used to apply the iontophoretic current to the users' skin as shown in FIG. 3.

The next block contains the detection and analysis circuitry. The signals generated through chemical reaction or spectrometry is continuously monitored here and compared against control sample readings. The actual quantity of the analyte extracted is computed with the help of calibration data provided by the controller. In addition the detection of analyte and the results of the analysis conducted over the patch as carried out by the controller and is computed with the help of calibration data available in the controller.

Another circuit block handles the storage of analytical data. This block utilises a micro SD card or any other suitable storage media for storing the analytical data. This data can later be transferred to a personal computer or any suitable device for further analysis.

The support material for transdermal patch is made up of a thin flexible sheet made of polymer, or rubber, or resin, or textile, or medicated foam or a thin metal acceptable for medical applications, At least a part of the support material will have some kind of adhesive to stick it to the skin. The patch can be of any shape as desired by the user. It can be in the shape of a tattoo for giving an aesthetic look to the patch.

The patch is attached to the patient's skin using adhesives or a strap or both.

The extracted body fluid may be collected in a reservoir of the transdermal skin patch. The reservoir of the patch is in contact with the biological membrane. The reservoir can be a wearable cell, a membrane, an absorbent strip, a hydrogel, or a structure that performs an equivalent function. The reservoir of the transdermal patch contains at least one reagent in order to detect the presence of certain analytes in the body fluid that has been extracted from or through the biological membrane. In one embodiment, the hydrogel layer of the reservoir may contain the reagents, and the reagents are attached to the hydrogel by ionic and/or covalent means, or may be immobilized by gel entrapment. The reagents may also be arranged as an adjacent layer to the hydrogel wherein the analyte from the body fluid that has been extracted into the hydrogel can diffuse into and react to generate by-products. The by-products are then being detected using electrochemical, biochemical, optical, fluorescence, absorbance, reflectance, Raman, magnetic, mass spectrometry, IR spectroscopy measurement methods and combinations thereof.

As per one of the aspect of the present invention, the present disclosed analyte extraction and detection system include a patch which comprises at least one active reservoir for holding a detection formulation containing reagent of the specific analyte extracted transdermally from a patient.

The active reservoir should have one or more orifices for smooth passage of the extracted analyte for interaction with the reagent present in the formulation. The active reservoir, with formulations containing reagents, is configured for a steady or intermittent detection of analytes. The same active reservoir is designed for multiple usages.

In another exemplary embodiment the reservoirs may be empty and/or filled with a hydrogel or semisolid formulation or absorbent pad without any reagent for the collection of analytes onto them. In such cases the reservoir cells are designed so that the analyte once collected cannot leak/spill on the patch or back onto the skin and can be collected whenever desired for analysis outside.

In yet another embodiment there is provided a plurality of reservoirs configured for holding the formulation and also collecting the samples of the analytes extracted transdermally. The patch can deliver the analyte to the detection formulation when the patch is on the patient's skin. There can be a plurality of active reservoir cells and the detection can be programmed/scheduled accordingly with the help of controller. The patch contains a tab, which connects to the controller. The reservoir cells are piled/stacked one under the other and/or placed adjacent with one another so that the said formulation is available to the analyte for a longer period of time and for the multiple detection of the said analyte. Also on requirement the plurality of the active cells are activated simultaneously by the controller by activating the electrodes for performing the mixing of the different formulations and/or otherwise.

In another embodiment the said formulations may contain at least one among chemical permeation enhancers, osmotic agents, other formulation additives like cross linking agents, humectants, anti microbial agents, chelating agents and may also contain some ions and counter ions, but not limited to as desired.

The patch is designed in such a way that when it is attached to the skin, the energy transducers are very close to the skin. The reservoir is so designed that they remain in contact with the conductive electrodes. Generally, a thin layer of the detection formulation in the form of gel and or in other desired form is available in the reservoir of the active transdermal patch and it is sandwiched between the skin and the transducers, when the active transdermal patch is attached to the skin. Further the transducers are connected to the controller and are configured to operate in isolation and/or simultaneously; it is preprogrammed (as described later) that will not in any way can make any damage to the skin. When current passes through the transducers and are activated by the controller, the formulation contained in the reservoir comes in contact with the analyte extracted through the skin in a controlled manner.

As per one of the embodiment of the present invention the controller is configured for activating the plurality of energy sources simultaneously with respect to the different active cells so as to perform the controlled extraction followed by controlled detection of the extracted analyte. Still further embodiment of the present invention discloses the provision of providing the different combinations of formulations present in a plurality of reservoirs, which can come in contact with the extracted analyte simultaneously.

It is also possible to analyze multiple analytes simultaneously, in parallel, or in series. The results from these multiple analyses may be used in combination with algorithms, for example, to increase the accuracy, or precision, or both, of the analysis and measurements.

It is also possible to remove the patch/reservoir from contact with the biological membrane in order to analyze the collected body fluid. In another embodiment, the reservoir may remain in contact with the biological membrane when the collected body fluid is analyzed.

The controller is placed in a housing, and has an opening to accommodate the inserted patch. The housing also has connection arrays of electric terminals to which the control circuitry and power source are electrically connected through electrical connectors, and are preferably mounted with the electric circuits on a printed circuit board. The plural, spaced apart electrical terminals electrically connect to the respective energy sources. While, the plural, spaced apart electrical terminals electrically connect the power source and electrical connectors to the control circuitry. Further, it may be appreciated that the patch insertion and release mechanisms may take any known form, so long as the patch tab is capable of being mechanically and electrically connected to and disconnected from the controller.

In another embodiment, the controller further includes a display, such as an LCD display. Other suitable displays may be provided. The controller may provide an interface that allows information be downloaded to an external device, such as a computer. Such an interface may allow the connection of interface cables, or it may be a wireless interface.

The detection methods are performed by a controller. As an example to the disclosure, the controller may be configured to determine body fluid glucose concentration by incorporating glucose oxidase in the medium of patch. Glucose from extracted body fluid reacts with glucose oxidase to generate hydrogen peroxide. Hydrogen peroxide may be detected by the oxidation of hydrogen peroxide at the surface of electrodes incorporated into the patch. The oxidation of hydrogen peroxide transfers electrons onto the electrode surface which generates a current flow that can be quantified using a potentiostat incorporated into the controller. A glucose concentration proportional to the concentration of hydrogen peroxide may be calculated and the result be reported to the user via a display. Various configurations of electrodes and reagents, known to those ordinary skill in the art, may be incorporated to perform detection and analysis of glucose and other analytes.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

The invention claimed is:

1. An active transdermal analyte extraction system for extraction of body analytes through a biological membrane of a subject, the system comprising:
  a non-invasive transdermal patch without microneedle arrays, the patch configured to be attached to a skin of the subject, wherein the patch includes three energy treatment transducers consisting of:
    a thermal transducer;
    an ultrasonic transducer;
    an electromotive force transducer; and
  a reservoir configured to collect an extracted body analyte;
  a controller operatively connected to each of the transducers, wherein the controller comprises a programmable microprocessor configured to pulse the three energy treatments sequentially or simultaneously together, comprising pulsing heat in a range of 30-60° C., pulsing ultrasonic vibrations in a frequency range of 20 KHz-25 KHz, and pulsing an electromotive force in a range of 0.01 mA-10 mA to the skin of the subject to extract a body analyte through the skin of the subject into the reservoir, wherein the pulses vary in intensity, sequence, and timing and are applied in tandem sequentially or simultaneously; and
  one or more sensors for delivering feedback to the controller.

2. The active transdermal analyte extraction system as claimed in claim 1, wherein the patch is configured to detect the extracted body analyte using one or more of chemical, electrical and optical methods.

3. The active transdermal analyte extraction system as claimed in claim 1, wherein the programmable microprocessor is preprogrammed for detecting a targeted body analyte.

4. The active transdermal analyte extraction system as claimed in claim 1, wherein the reservoir comprises a formulation configured to react with the extracted body analyte and to provide a measurable result.

5. The active transdermal analyte extraction system as claimed in claim 4, wherein the formulation comprises enzymes and chemicals capable of reacting with the extracted body analyte to provide a measurable result.

6. The active transdermal analyte extraction system as claimed in claim 1, wherein the reservoir is in direct contact with the electromotive force transducer.

7. The active transdermal analyte extraction system as claimed in claim 4, wherein the formulation comprises polymers, co-polymers, cross linking agents, humectants, chemical permeation enhancers, anti-microbial agents, chelating agents, ions, counter ions, or a combination of any of the foregoing.

8. The active transdermal analyte extraction system as claimed in claim 1, wherein the patch comprises a plurality of electrodes configured to extract the body analyte and to detect the extracted body analyte.

9. The active transdermal analyte extraction system as claimed in claim 1, wherein the patch comprises a membrane layer configured to allow selective transport of the extracted body analyte.

10. The active transdermal analyte extraction system as claimed in claim 1, wherein the patch comprises a protective liner, a coating or a seal configured to be removed before application of the patch to the skin of the subject.

11. The active transdermal analyte extraction system as claimed in claim 1, comprising an input power source operably connected to each of the transducers, wherein the input power source is selected from a battery, an AC power adaptor, a capacitor, and a combination of any of the foregoing.

12. The active transdermal analyte extraction system as claimed in claim 11, wherein the input power source is configured to deliver current in a range of 0.01 mA-1000 mA.

13. The active transdermal analyte extraction system as claimed in claim 11, wherein the input power source is configured to deliver potential in a range of 0 to 12 V DC.

14. The active transdermal analyte extraction system as claimed in claim 1, wherein the ultrasonic transducer comprises a piezoelectric device.

15. The active transdermal analyte extraction system as claimed in claim 1, wherein the ultrasonic transducer comprises a plurality of piezoelectric devices configured to deliver ultrasonic vibrations in a frequency range of 20 KHz-25 KHz.

16. The active transdermal analyte extraction system as claimed in claim 1, wherein the thermal transducer comprises a plurality of electrically conductive coatings configured to generate and transfer heat to the skin of the subject.

17. The active transdermal analyte extraction system as claimed in claim 1, wherein the controller is configured to simultaneously pulse the heat, the ultrasonic vibrations, and the electromotive force, wherein the pulse is characterized by a duration of 1 millisecond or more.

18. The active transdermal analyte extraction system as claimed in claim 1, wherein a sequence and a duration of the pulses are optimized according to a required detection accuracy.

19. The active transdermal analyte extraction system as claimed in claim 1, wherein the patch comprises a support material, wherein,
the support material is selected from a polymer, a rubber, a resin a textile, and a metal; and
at least a part of the support material comprises an adhesive configured to attach the patch to the skin of the subject; and
at least a part of the support material is perforated.

20. The active transdermal analyte extraction system as claimed in claim 1, wherein the programmable microprocessor is configured to control temperature, rate of heating, duration of heating, ultrasonic energy, ultrasonic frequency, ultrasonic intensity, ultrasonic duration, and electromotive energy.

21. The active transdermal analyte extraction system as claimed in claim 1, wherein the controller comprises a display.

22. The active transdermal analyte extraction system as claimed in claim 1, wherein the controller comprises a memory and a wireless interface.

23. The active transdermal analyte extraction system as claimed in claim 1, comprising a patch insertion and release mechanism configured to mechanically and electrically connect and disconnect the patch from the controller.

24. A method for performing transdermal extraction, detection, and analysis of a body analyte using an electronic patch, the method comprising:
attaching an electronic patch to a skin of a subject, wherein the electronic patch includes a non-invasive transdermal patch without microneedle arrays and three energy treatment transducers, consisting of:
a thermal transducer;
an ultrasonic transducer;
an electromotive force transducer; and
a reservoir configured to collect an extracted body analyte;
inputting electrical energy from a power source to the thermal transducer, the ultrasonic transducer, and the electromotive force transducer to pulse heat in a range of 30-60° C., pulse ultrasonic vibration in a frequency range of 20 KHz-25 KHz, and pulse electromotive force in a range of 0.01 mA-10 mA to the skin of the subject, wherein the pulses vary in intensity, sequence, and timing and are applied in tandem sequentially or simultaneously;
controlling the electrical energy power input using a controller; and
extracting a body analyte through the skin of the subject to the reservoir; and
analyzing the extracted body analyte.

25. The method as claimed in claim 24, wherein the patch is configured to analyze the extracted body analyte using one or more chemical, electrical and optical methods.

26. The method as claimed in claim 24, wherein the body analyte is selected from glucose, lithium, sodium, potassium, calcium, toxins, cholesterol, insulin, therapeutic and pharmacologic agents, drugs of abuse, amino acids, blood gases, enzymes, antibiotics, and cytokines.

27. The method as claimed in claim 24, wherein the controller comprises a microprocessor which is preprogrammed for analysis of a targeted body analyte.

28. The method as claimed in claim 24, wherein analyzing the extracted body analyte comprises reacting the extracted body analyte with a formulation comprising polymers, copolymers, cross linking agents, humectants, chemical permeation enhancers, anti microbial agents, chelating agents, ions, or counter ions.

29. The method as claimed in claim 28, wherein,
the formulation is configured to react with the extracted body analyte to provide a reacted formulation; and
the reacted formulation provides a measurable result.

30. The method as claimed in claim 28, wherein the formulation comprises enzymes or chemicals reactive with the extracted body analyte and that upon reaction produces a measurable result.

31. The method as claimed in claim 24, wherein the thermal transducer, the ultrasonic transducer, and the electromotive force transducer are simultaneously pulsed, wherein the pulses are characterized by a duration of 1 millisecond or more.

32. An active transdermal analyte extraction system for extraction of body analytes through a biological membrane, the system comprising:
a non-invasive transdermal patch without microneedle arrays, the patch configured to be attached to a skin of a subject, wherein the patch includes three energy treatment transducers consisting of:
a thermal transducer configured to deliver heat to the skin in a temperature range of 30-60° C.;
an ultrasonic transducer configured to deliver ultrasonic vibrations in a frequency range of 20 KHz-25 KHz to the skin;
an electromotive force transducer configured to deliver current in a range of 0.01 mA-10 mA to the skin; and
a reservoir configured to collect an extracted body analyte;
a controller operatively connected to each of the transducers,
wherein the controller comprises a programmable microprocessor configured to simultaneously or sequentially apply pulses of heat, ultrasonic vibrations, and an electromotive force to the skin of the subject to extract a body analyte through the skin of the subject into the reservoir, wherein the pulses vary in intensity, sequence, and timing; and
one or more sensors for delivering feedback to the controller.

* * * * *